(12) United States Patent
Parrott

(10) Patent No.: US 10,228,321 B1
(45) Date of Patent: Mar. 12, 2019

(54) SYSTEM AND METHOD FOR INFRARED REFLECTION AVOIDANCE

(71) Applicant: Saudi Arabian Oil Company, Dhahran (SA)

(72) Inventor: Brian Parrott, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/820,068

(22) Filed: Nov. 21, 2017

(51) Int. Cl.
*G01N 21/01* (2006.01)
*G01N 21/952* (2006.01)

(52) U.S. Cl.
CPC ........... *G01N 21/01* (2013.01); *G01N 21/952* (2013.01); *G01N 2021/0112* (2013.01); *G01N 2201/0642* (2013.01)

(58) Field of Classification Search
CPC ................................ G01N 25/72; G01N 21/01
See application file for complete search history.

(56) References Cited

U.S. PATENT DOCUMENTS

| | | | |
|---|---|---|---|
| 6,236,044 B1* | 5/2001 | Chou | G01N 21/8806 250/330 |
| 9,066,028 B1* | 6/2015 | Koshti | H04N 5/33 |
| 2003/0080297 A1* | 5/2003 | Bales | G01N 21/8806 250/353 |
| 2003/0193987 A1* | 10/2003 | Zalameda | G01J 5/62 374/5 |
| 2010/0100275 A1* | 4/2010 | Mian | G01M 17/013 701/31.4 |
| 2015/0260667 A1* | 9/2015 | Isakov | G01N 25/72 374/5 |
| 2017/0176343 A1* | 6/2017 | Krishnan | G01N 21/952 |

* cited by examiner

*Primary Examiner* — Yara B Green
(74) *Attorney, Agent, or Firm* — Leason Ellis LLP

(57) ABSTRACT

A method for protecting an inspected structure from external infrared emissions comprises shielding the inspected structure using a protective sheet so as to block infrared emissions from an external infrared radiation source from reaching the inspected structure, positioning the at least one protective sheet using at least one support so as to block a maximal amount of radiation from the external radiation source, and capturing infrared radiation from the inspected structure using an infrared camera.

16 Claims, 7 Drawing Sheets

SYSTEM AND METHOD FOR INFRARED REFLECTION AVOIDANCE

FIELD OF THE INVENTION

The present invention relates monitoring of corrosion using infrared radiation capture, and in particular, relates to a system and method for protecting monitored structures from external sources of infrared radiation so that accurate measurements of infrared radiation emitted by the structures can be obtained.

BACKGROUND OF THE INVENTION

In the oil and gas industry, infrastructural corrosion (e.g., pipe corrosion) is a major problem responsible for significant costs. As pipes and vessels are typically covered with insulating or covering layers, such as aluminum cladding, corrosion occurring beneath the insulation (CUI) is not evident upon visual inspection, and other non-visual monitoring methods are required to determine whether or not corrosion is present. Infrared inspection is a promising technology for monitoring CUI, as infrared radiation corresponding to internal temperature contrasts can pass through the insulation and can be detected using infrared cameras. The temperature contrasts obtained are indicative of moisture build-up and CUI.

It has been found that while infrared-based monitoring can accurately determine whether CUI is present in an inspected structure, infrared-based monitoring is sensitive to interfering radiation coming sources external to the inspected structure. For example, substantial radiation interference can come from heated objects in the area of the inspected structure, such as nearby concrete and asphalt. The infrared radiation emitted by these sources is typically reflected by the aluminum cladding used on pipes. These reflections can be quite significant in comparison to emissions coming from the inspected structure through the aluminum cladding. This extraneous radiation makes it more difficult to pick up the sometimes subtle temperature contrasts that reveal CUI.

What is therefore needed is a system and method that reduces this extraneous radiation so that the benefits of infrared-based CUI inspection can be more fully realized.

SUMMARY OF THE INVENTION

Embodiments of the present invention provide a method for protecting an inspected structure from external infrared emissions. The method comprises shielding the inspected structure using a protective sheet so as to block infrared emissions from an external infrared radiation source from reaching the inspected structure, positioning the protective sheet using at least one support so as to block a maximal amount of radiation from the external radiation source, capturing infrared radiation from the inspected structure using an infrared camera, monitoring the amount of infrared radiation from the external radiation source using the captured image using the camera, and repeating the positioning step until a minimal amount of infrared radiation is received from the external radiation source In some implementations, the external radiation source is the ground below the inspected structure, and the protective sheet is positioned on or over the ground and underneath the inspected structure.

Certain embodiments of the method of the present invention further comprise disposing a plurality of protective sheets to protect the structure from ground emissions and at least one protective sheet to protect the structure from emissions from another heated item in the vicinity of the structure. In other embodiments, the method further comprises disposing a plurality of protective sheets to fully enclose the inspected structure with the exception of a small opening for an aperture of the infrared camera.

In some implementations, the protective sheet includes an infrared reflective layer positioned to face the infrared radiation source, a diffuse fabric layer positioned to face the inspected structure, and an insulating layer positioned between the infrared reflective layer and the diffuse fabric layer. The infrared reflective layer can be made from Mylar.

Embodiments of the present invention also provide a system for protecting an inspected structure from external infrared emissions. The system comprises an infrared camera positioned to capture infrared radiation from the inspected structure, a protective sheet positioned to block infrared emissions from an external infrared radiation source from reaching the inspected structure, and at least one support coupled to the protective sheet, wherein the support holds and orients the protective sheet in the position so as to block a maximal amount of radiation from the external radiation source. In some implementations, a plurality of protective sheets fully enclose the inspected structure and have an opening for an aperture of the infrared camera.

In some implementations, the external radiation source is the ground below the inspected structure, and the at least one protective sheet is positioned over the ground and underneath the inspected structure. The protective sheet can be suspended over the ground using at least one spacer. This helps to prevent conductive heat transfer between the ground and the sheet, thus minimizing the potential that the sheet becomes a significant source of infrared radiation.

The system according to the present invention can also comprise a plurality of protective sheets disposed to protect the structure from ground emissions and at least one protective sheet disposed to protect the structure from emissions from another heated item in the vicinity of the structure. The system can further comprise an additional protective sheet for protecting the infrared from sunlight.

In certain embodiments, the protective sheet includes an infrared reflective layer positioned to face the infrared radiation source, a diffuse fabric layer positioned to face the inspected structure, and an insulating layer positioned between the infrared reflective layer and the diffuse fabric layer. The infrared reflective layer can be made from Mylar.

These and other features can be appreciated from the accompanying description of certain embodiments of the invention which are discussed in relation to the accompanying drawing figures.

DETAILED DESCRIPTION CERTAIN OF EMBODIMENTS OF THE INVENTION

Detecting corrosion under insulation (CUI) on structures in the field non-destructively (i.e., without removing the insulation or dissembling the structure) can be challenging. Infrared thermography is a promising technique for detection of CUI because regions of a structure containing corrosion and/or moisture respond to external heating at different rates from surrounding non-corroded material. This heating differential creates temperature contrasts and differential infrared emission patterns. As infrared radiation can penetrate through structural insulation and/or cladding, the temperature contrasts can be detected using an infrared camera. However, as the contrasts can be subtle, it is important for the radiation captured by the infrared camera to accurately reflect only the infrared radiation emitted from the area of focus, and not extraneous infrared radiation received from other sources. It is thus important to protecting the area of focus, and possibly the infrared camera itself, from such extraneous infrared radiation to achieve accurate CUI detection.

Figure 1:
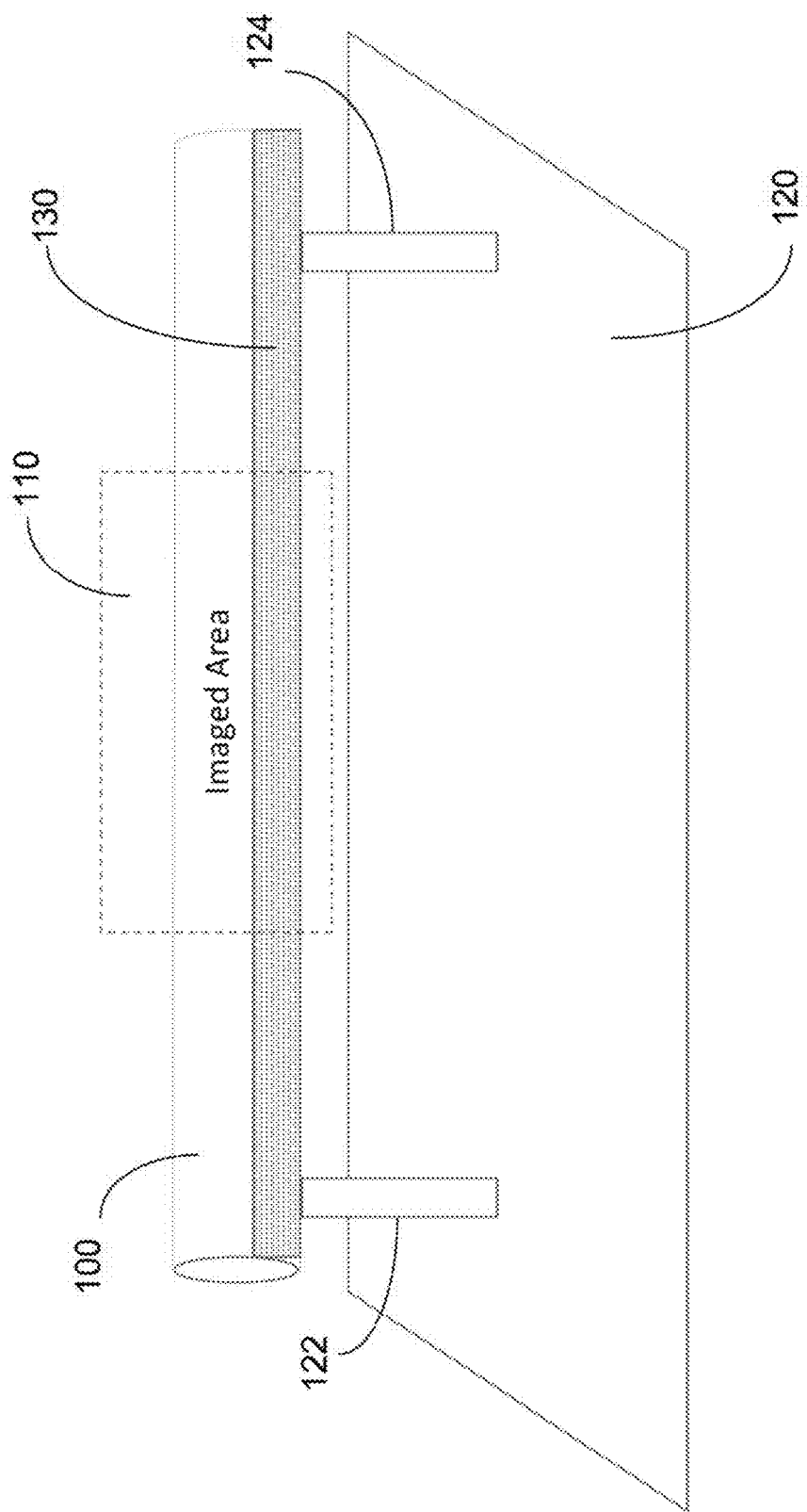
FIG. 1 is a schematic perspective view of an inspected structure (in the example shown, a pipeline) subject to infrared reflection from external sources according to the prior art.

FIG. 1 illustrates an exemplary structure under investigation that is exposed to infrared radiation from external sources, which interferes with infrared imaging. A structure 100, which in this case is a hollow pipe, includes an imaged area 110 that is to be inspected for CUI by an infrared imaging device (not shown in FIG. 1, but to be understood as being in front of the view as illustrated). The surface of the structure 100 can comprise an aluminum cladding or another material that is reflective with respect to infrared radiation. The structure 100 is suspended above the ground 120 by supports 122, 124. The ground 120 can comprise concrete or similar materials emit significant amounts of infrared radiation even at ambient temperatures. The ground 120 can therefore act as a source of infrared radiation, part of which is directed to the structure 100 and reflected from the structural cladding. The shaded area 130 on the bottom of the structure indicates a region from which infrared radiation, originating from the ground 120, is being reflected toward the viewing camera. The radiation reflected from area 130 can overwhelm radiation related to CUI emitted from the structure, and obscure any CUI that is present.

Figure 2:
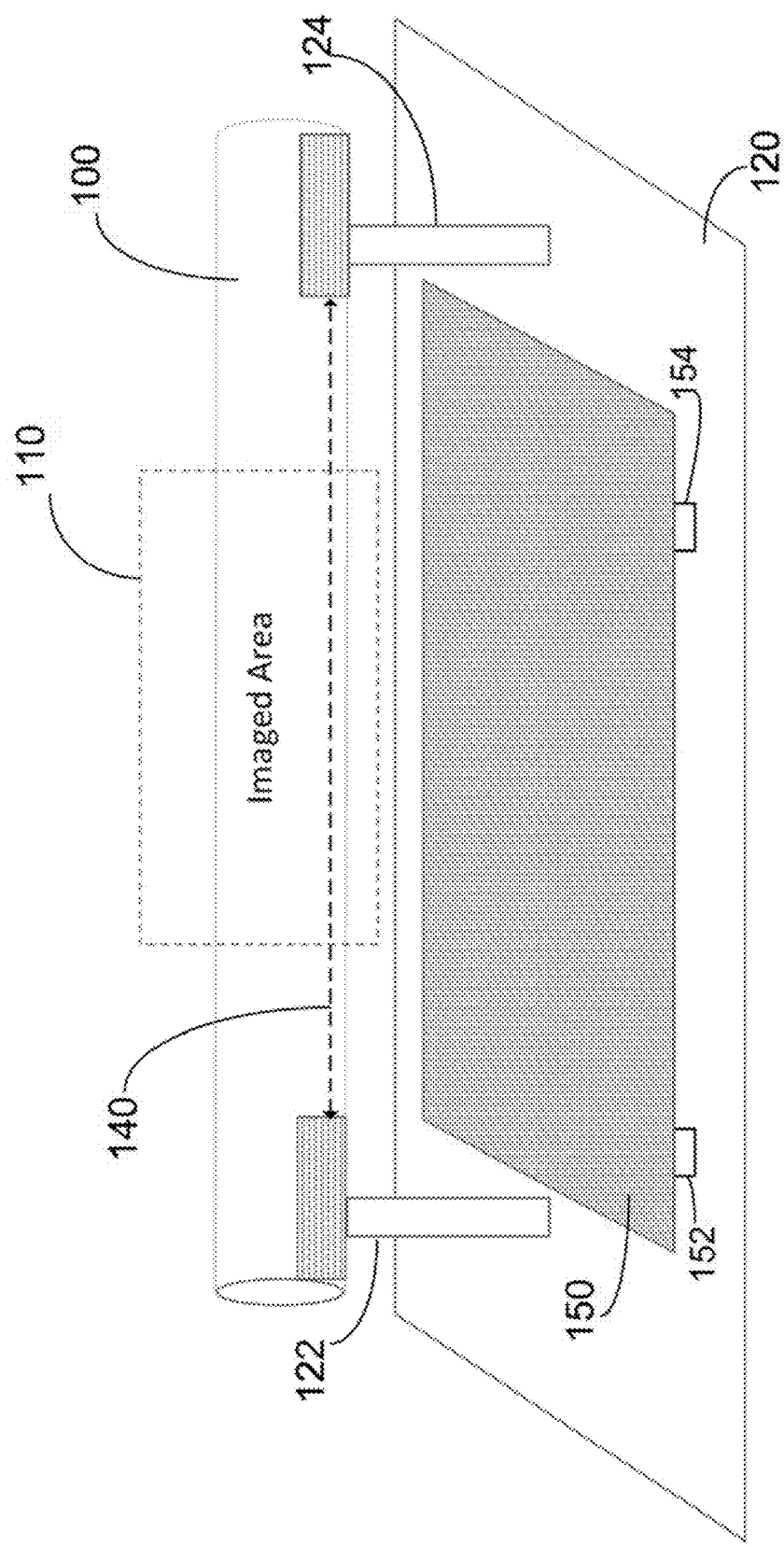
FIG. 2 is a schematic perspective view of an inspected structure, similar to the structure shown in FIG. 1, being protected from external infrared radiation according to an embodiment of the present invention.

FIG. 2 illustrates a similar exemplary structure under investigation. In this example, a protective sheet 150 is positioned over the ground 120 underneath the structure 110. The protective sheet 150 is made of a non-emissive material that blocks infrared radiation emanating from the ground 120 from reaching the structure 130. As illustrated, the section 140 on the bottom of structure 100 that is directly above the protective sheet is not shaded, indicating that this section is not exposed to infrared radiation from the ground, and consequently does not reflect such radiation. Thus, in the example shown, the protective sheet 150 functions to remove a significant source of external infrared radiation that could obfuscate CUI detection. In some embodiments, to prevent the protective sheet from heating by contact with the ground and becoming a source of infrared radiation as a result, spacers 152, 154 can be placed underneath the protective sheet 150 to prevent direct contact and conductive heat transfer between the ground and the protective sheet. The size of the protective sheet 150 shown in FIG. 2 is merely illustrative, and in actual embodiments the protective sheet can be as large as necessary to protect the structure from ground emissions radiated at an angle to the surface (i.e., as opposed to radiation emitted directly or at a normal angle to the surface of the structure).

Figure 3:
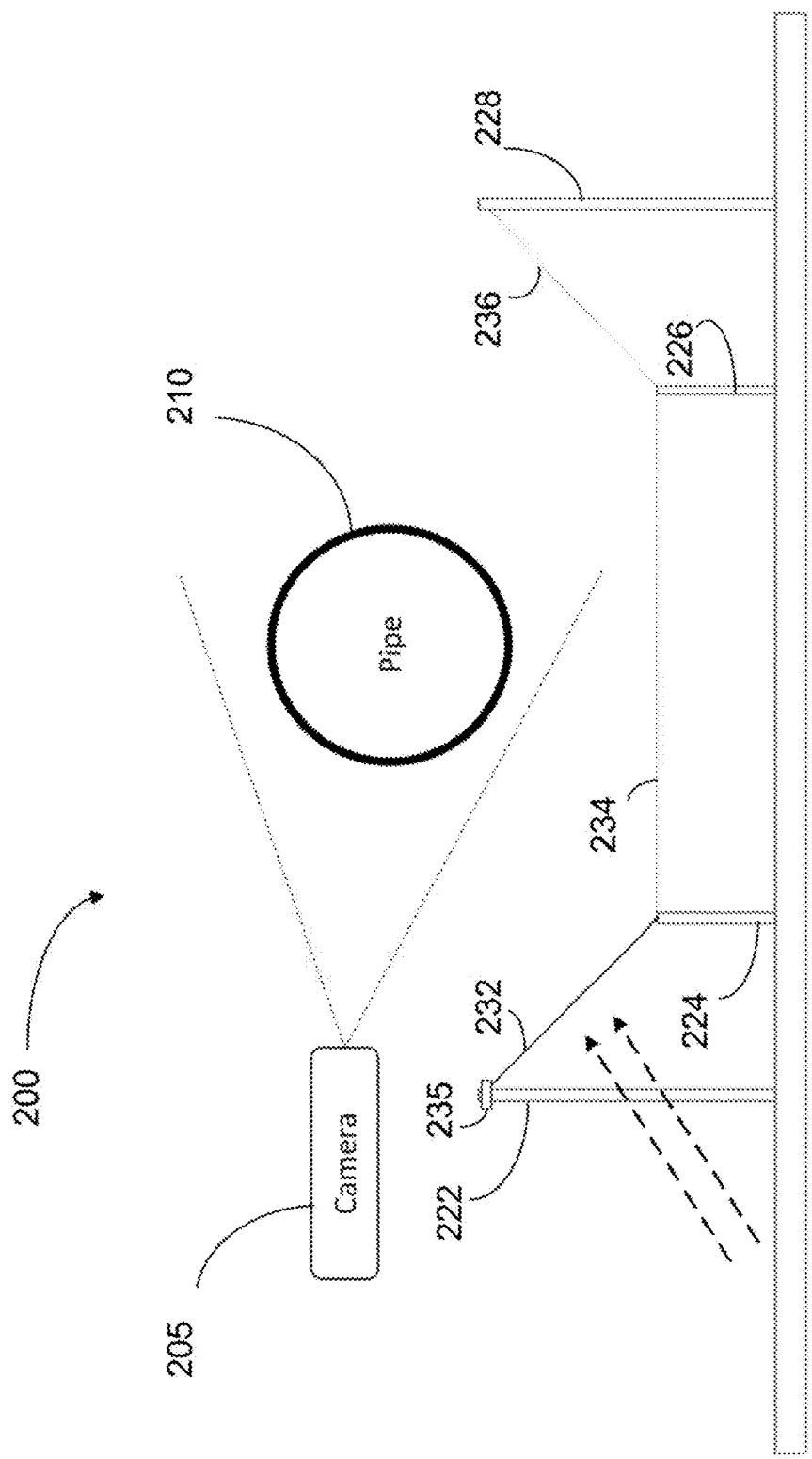
FIG. 3 is a side view of an arrangement of a system for protecting an inspected structure from external radiation according to the present invention.

FIG. 3 is a side view of an exemplary arrangement 200 for protecting an inspected structure from external infrared emissions according to the present invention. In the arrangement 200, an infrared camera 205 is oriented so as to capture infrared radiation emanating from a structure 210, which in the example shown, is a pipe. A group of horizontally-spaced supports 222, 224, 226, 228 is installed on the ground 220 beneath an inspected structure 210. A first protective sheet 232 extends between supports 222 and 224, a second protective sheet 234 extends between supports 224 and 226, and a third protective sheet 236 extends between supports 226 and 228. As shown, protective sheets 232, 236 are oriented at an angle with respect to the horizontal so as to better protect the structure from infrared radiation emitted from the ground toward the structure at angle indicated by the dotted arrows. Protective sheet 234 is oriented horizontally to covers the entire area directly underneath the structure. Together, supports 222, 224, 226, 228 and protective sheets 232, 234, 236 fully protect the structure from infrared emissions from the ground source. While the supports are shown as having linear and/or cylindrical shapes, the supports can have other shapes, and can include flares and flanges for attachments of material, without limitation. The supports are made from a non-IR-emissive material, such as aluminum. The protective sheets, e.g., 232, can be secured to the supports, e.g., 222, by a grip 235, such as a clamp, elastic band or other similar fixture. In addition, the protective sheet can include grommets, to enable the sheets to be easily secured to other structure.

Figure 4:
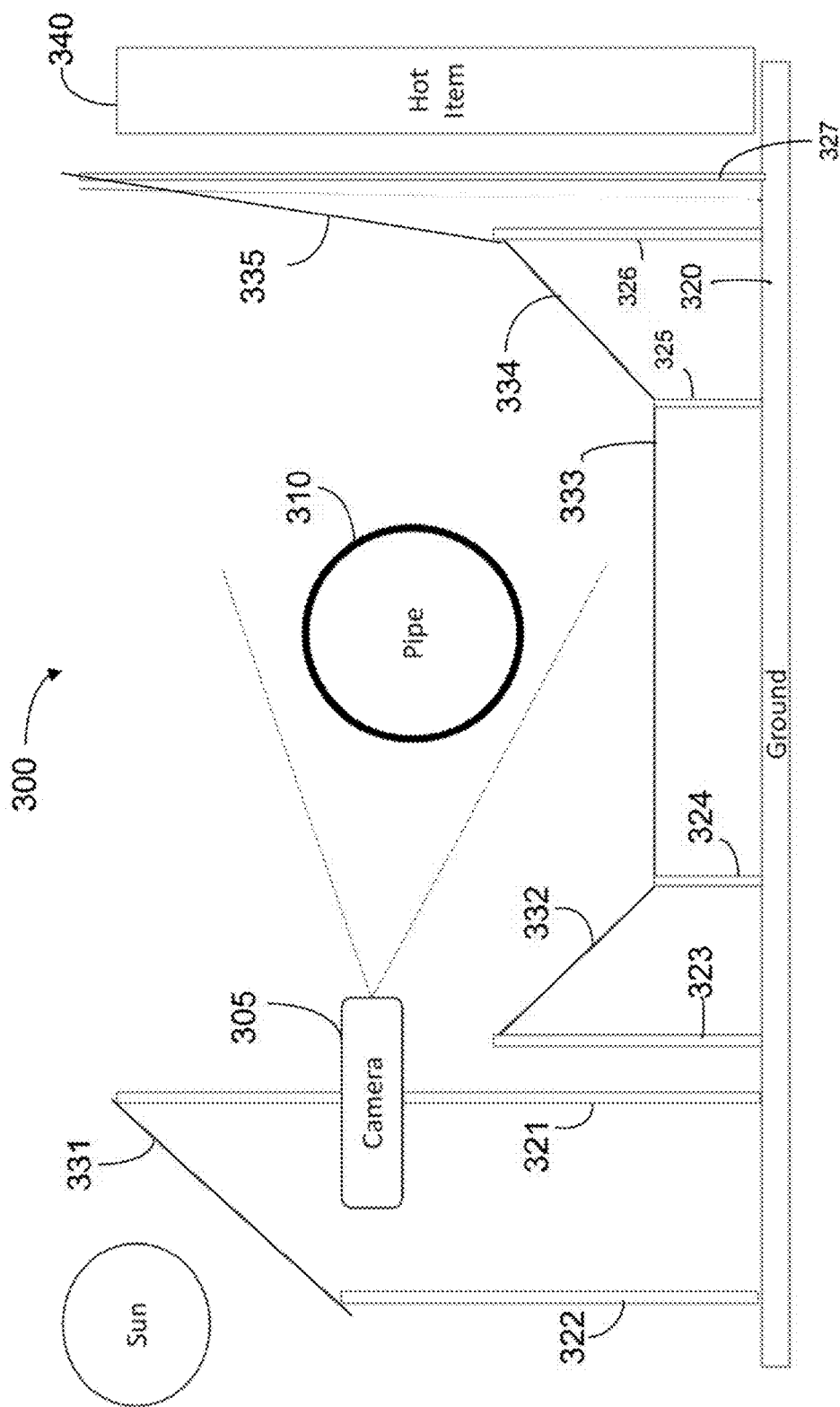
FIG. 4 is a side view of another arrangement of a system for protecting an inspected structure from external radiation according to the present invention.

In some field applications, the ground is not the only object that can emit infrared radiation toward the inspected structure. FIG. 4 is a side view of another arrangement of a system for protecting an inspected structure from additional sources of infrared radiation. In the arrangement 300, an infrared camera 305 is similarly oriented to capture infrared emanating from a structure 310. In this example, in addition to the ground 320, both the sun and a nearby heated object 340, such as a wall, are additional sources of infrared radiation. In the arrangement, several supports and protective sheets are positioned to block these sources from reaching either the camera 205 or the structure 210. For example, a camera support 321 which fixes the position of the infrared camera with respect to structure 210, and additional support 322, couple to a protective sheet 331 which extends between the supports and is angled so as to protect the infrared camera 205 and structure 210 from overexposure to sunlight, which could negatively impact the accuracy of infrared detection. Protective sheets 332, 333 and 334 which extended from respective pair of supports 323/324, 324/325, and 325/326, protect the structure from ground infrared emissions, in a similar configuration to that shown in FIG. 3. Another protective sheet 335 extends between supports 326 and 327, positioned most distally from the camera 305. Protective sheet 335 blocks infrared radiation emitted from heated object 340.

Figure 5:
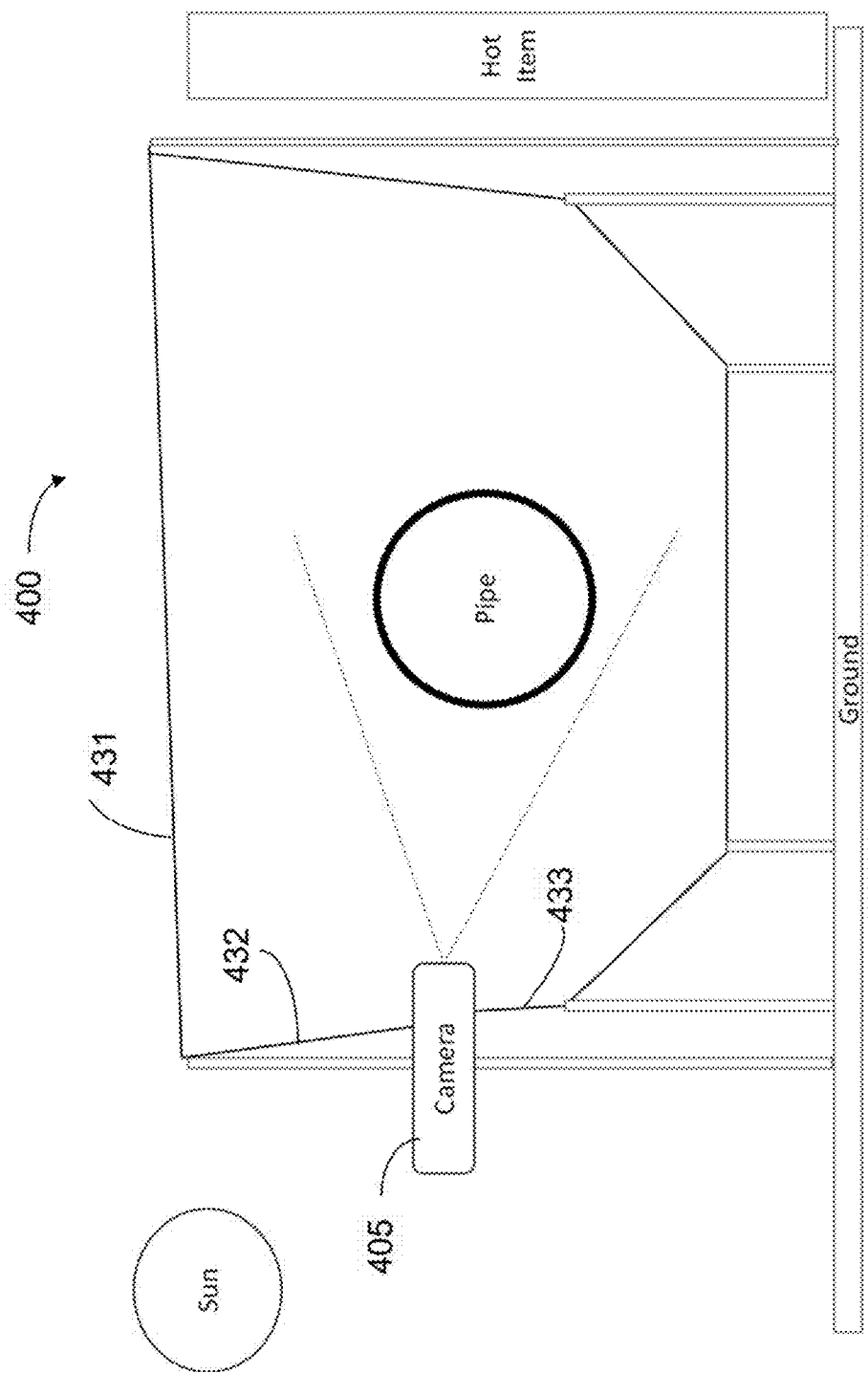
FIG. 5 is a side view of yet another arrangement of a system for protecting an inspected structure from external radiation according to the present invention.

FIG. 5 shows another arrangement in which the protective sheets fully enclose the inspected structure to further ensure that little external infrared radiation reaches the inspected structure. In pertinent part, in arrangement 400, a top protective sheet 431 extends between the most proximal and distal supports over the inspected structure. Protective sheet 432 extends between the camera 405 and the top protective sheet 431, and another protective sheet 433 extended between the camera and a lower support. In this configuration, sunlight is blocked from reaching the inspected structure directly, and radiation from other sources of infrared radiation including the ground and heated objects similarly cannot reach the inspected structure directly. In the embodiment depicted a part of the camera 405 within the internal space enclosed by the protective sheet. In some instances, the camera itself can be a source of infrared radiation. For example, it is possible for parts of the camera to become heated and for such heated area to emit infrared radiation that is then reflected onto the sensor. In the arrangement shown in FIG. 5, penetration of the camera through the protective sheets is minimized to include only an opening capable of allowing the infrared radiation to pass into the camera lens while preventing IR light from penetrating around the camera lens.

Figure 6:
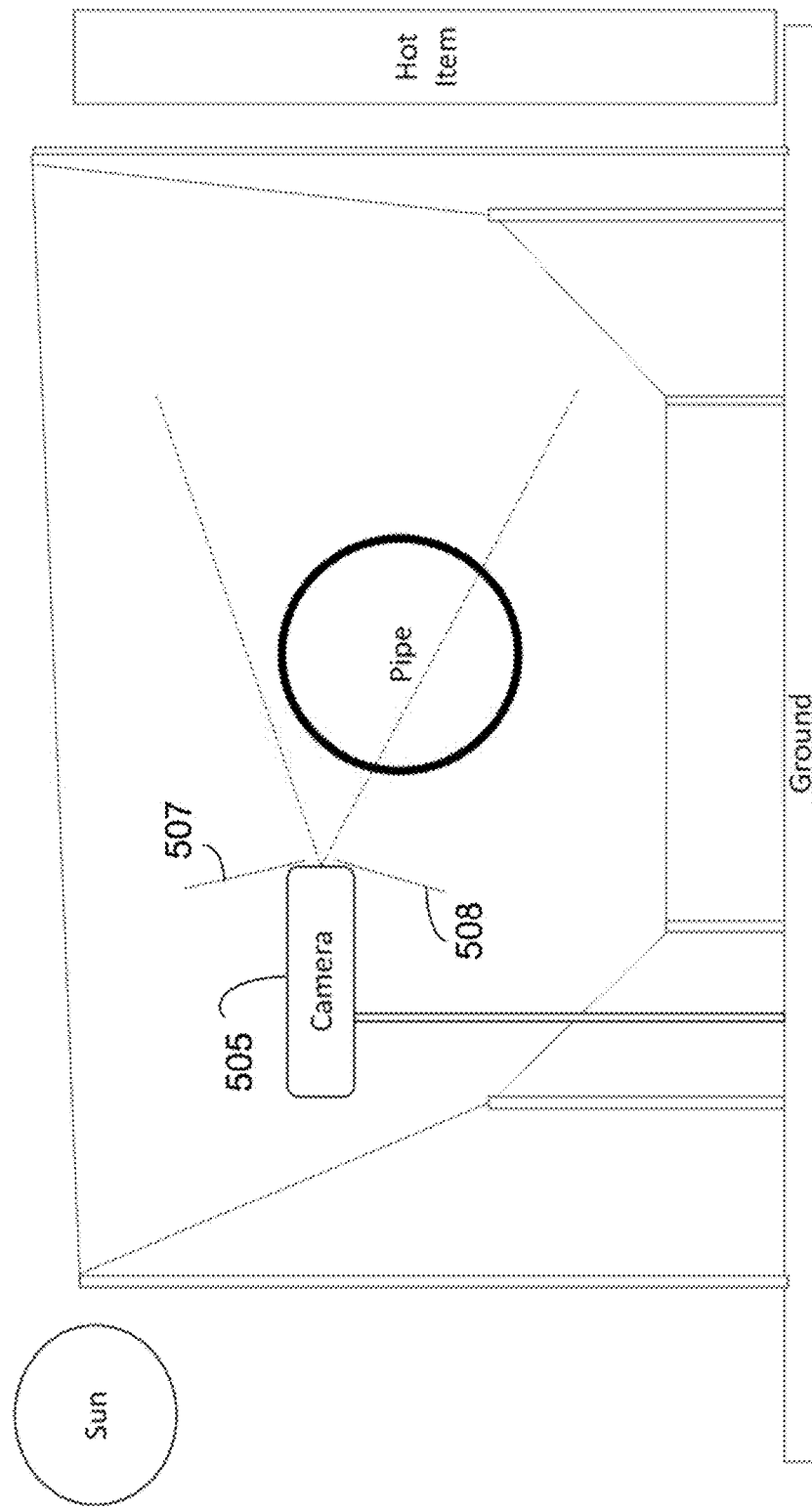
FIG. 6 is a side view of yet another arrangement of a system for protecting an inspected structure from external radiation according to the present invention.

FIG. 6 shows yet another arrangement which is similar to that shown in FIG. 5 in that in FIG. 6 the inspected structure is also enclosed by a plurality of protective sheets. In this embodiment the camera 505 is positioned entirely within the space bounded by the protective sheets. Accordingly, additional steps are taken so that the radiation produced by the infrared camera 505 itself does not reach the sensors of the camera. In the embodiment depicted, added protection is provided by additional protective structures 507, 508 are positioned on either side of the aperture of the infrared camera that block extraneous radiation from reaching the infrared sensors of the camera.

The infrared camera can be used to detect when an arrangement of protective sheets is working to sufficient block infrared reflections. In some implementations, as the protective sheets are moved iteratively into different positions (e.g., manually), an observer can use the camera to monitor at each iteration whether the then-current positions of the protective sheets sufficiently block infrared reflections and minimize infrared obstructions until arrangement has been reached in which infrared reflections have been reduced to a satisfactory level. If it is found that the protective sheets in use do not sufficiently minimize infrared reflections, additional protective sheets can be added until sufficient minimization occurs.

The composition and structure of the protective sheets can be implemented using a variety of different forms. The protective sheets can be made wholly or in part of an infrared-reflective material (i.e., a material that is a poor infrared absorber and emitter). In a simple implementation, the protective sheets can be made of aluminum or other infrared-reflective metal. Alternatively, the protective sheets can be layered in the manner of a metallized Mylar "space blanket" (Mylar is biaxially-oriented polyethylene terephthalate). It is most preferable for the protective sheets to be infrared-reflective on an external side to block incoming infrared radiation, and infrared-absorptive on the internal side (facing the inspected structure) to prevent infrared-reflections toward the inspected structure. For example, in a protective sheet made from metallized Mylar sheet, the metallic layer can be used on the externally-facing side, and the polymer material can be used on the reverse side.

Figure 7:
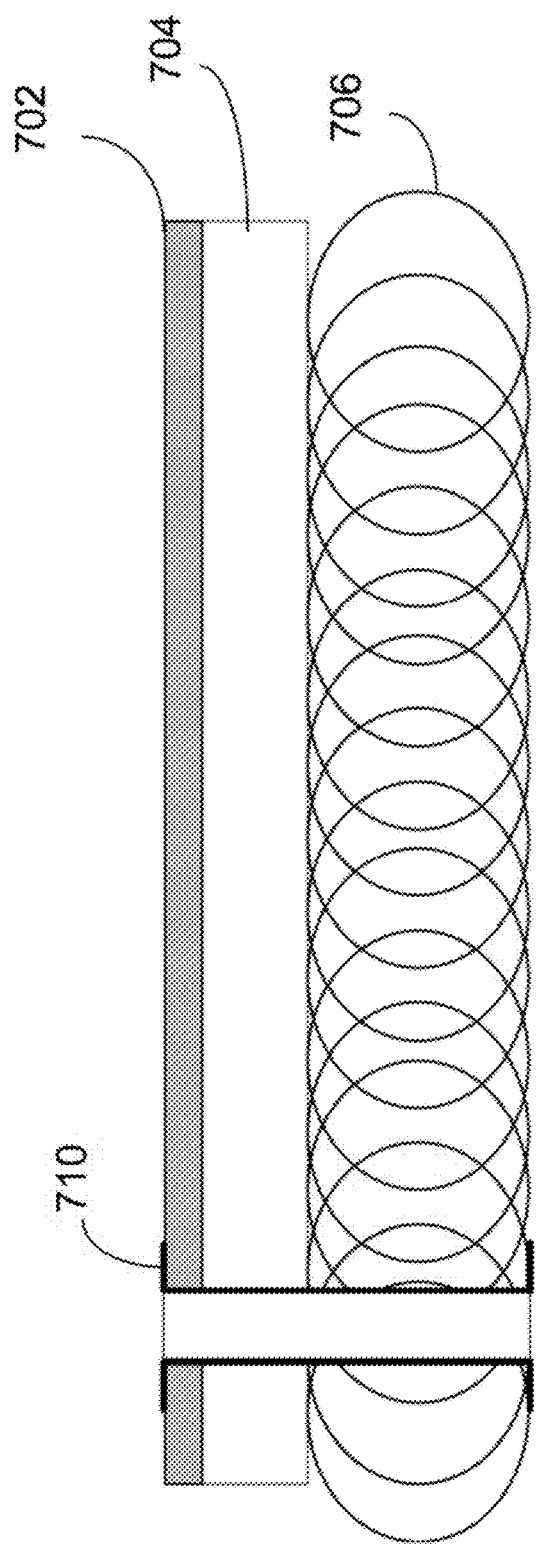
FIG. 7 is a schematic cross-section view of a material used for blocking infrared radiation according to an embodiment of the present invention.

FIG. 7 is a schematic illustration of the composition of an embodiment of a protective sheet according to the present invention. The protective sheet includes a thin metallic film or layer 702, a plastic layer coupled to the metallic film, and a diffuse fabric (e.g., wool-like) backing layer 706. The backing layer 706 can have a diffuse texture and preferably has low infrared reflectivity and low specific heat so that there is little internal energy to produce infrared radiation. The diffuseness of the backing layer also reduces the intensity of any internally-generated infrared radiation and produces a diffuse reflection. The protective sheet also includes one or more grommets e.g., 710 allowing for convenient attachment of the sheet to other structures. The grommet can secure the various layers of the protective sheet together. Alternatively, the protective sheet can be formed as a unitary structure.

Enhancements can include adding materials and coating to minimize emissions. Insulation can also be added to ensure that the surfaces of the protective sheets facing the inspected structure remain as cool as possible. It is possible to provide a nano-structured layer that prevents emissions of the specific wavelengths of infrared radiation for the infrared inspection technique. Alternatively, the materials can be nano-structured to limit emissions to a narrow bandwidth of low interest to the analysis of the structure of interest; this limited bandwidth can then be filtered from the image.

In some embodiments, the face of the sheet facing the object to be inspected can have a nano-structured pattern or set of layers that shifts the emission of blackbody radiation either towards visible light or further towards lower wavelength light such that the blackbody radiation of the sheet itself does not fall significantly within the infrared spectrum that is being measured with the camera, thus preventing the sheet from creating disruptive infrared emissions towards the object as the sheet heats up. These layers can shift the emitted wavelengths by being highly absorptive in the infrared spectrum and highly emissive in either the visible spectrum or the sub-infrared spectrum, thus shifting some emitted light out of the measured infrared spectrum. This could replace the diffuse fabric layer in some cases if it were determined to be favorable. However, it would likely suffer from some issues with reflectivity, so would likely be best used in cases where the sheet is enclosing the object almost entirely.

It is noted that after deploying the protective sheets, it can be advisable to include a wait time to allow the inspected structure to reach thermal equilibrium before infrared measurements are taken or analyzed. The amount of time can depend on the structure's material properties, paths for dissipation of heat, and the level of IR radiation to which it has been exposed, etc. The structure can be monitored with the infrared camera to determine when a sufficient level of equilibrium is reached.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for protecting an inspected structure from external infrared emissions comprising:
    shielding the inspected structure using a protective sheet so as to block infrared emissions from an external infrared radiation source from reaching the inspected structure;
    positioning the protective sheet using at least one support to block an amount of radiation from the external radiation source; and
    capturing infrared radiation from the inspected structure using an infrared camera;
monitoring the amount of infrared radiation from the external radiation source using the captured image using the camera; and
    repeating the positioning step until a minimal amount of infrared radiation is received from the external radiation source.

2. The method of claim 1, wherein the external radiation source is the ground below the inspected structure, and the protective sheet is positioned over the ground and underneath the inspected structure.

3. The method of claim 1, further comprising disposing a plurality of protective sheets to protect the structure from ground emissions and protective sheet to protect the structure from emissions from another heated item in the vicinity of the structure.

4. The method of claim 1, further comprising disposing a plurality of protective sheets to fully enclose the inspected structure with the exception of a small opening for an aperture of the infrared camera.

5. The method of claim 1, wherein the protective sheet includes an infrared reflective layer positioned to face the infrared radiation source, a diffuse fabric layer positioned to face the inspected structure, and an insulating layer positioned between the infrared reflective layer and the diffuse fabric layer.

6. The method of claim 5, wherein the infrared reflective layer is made from mylar.

7. A system for protecting an inspected structure from external infrared emissions comprising:
    an infrared camera positioned to capture infrared radiation from the inspected structure;
    a protective sheet positioned to block infrared emissions from an external infrared radiation source from reaching the inspected structure; and
    at least one support coupled to the protective sheet, wherein the support holds and orients the protective sheet in the position so as to block a maximal amount of radiation from the external radiation source.

8. The system of claim 7, wherein the external radiation source is the ground below the inspected structure, and the protective sheet is positioned over the ground and underneath the inspected structure.

9. The system of claim 8, wherein the protective sheet is suspended over the ground using at least one spacer.

10. The system of claim 7, wherein the protective sheet comprises a protective sheet layers disposed to protect the structure from ground emissions and a protective sheet disposed to protect the structure from emissions from another heated item in the vicinity of the structure, wherein at least one sheet layer is comprised of a material that differs from another sheet layer.

11. The system of claim 10, further comprising an additional protective sheet for protecting the infrared from sunlight.

12. The system of claim 7, wherein the protective sheet includes an infrared reflective layer positioned to face the infrared radiation source, a diffuse fabric layer positioned to face the inspected structure, and an insulating layer positioned between the infrared reflective layer and the diffuse fabric layer.

13. The system of claim 12, wherein the infrared reflective layer is made from mylar.

14. The system of claim 12, wherein the layers of the protective sheet are attached to one another at one or more locations, and wherein the protective sheet further comprises grommets which extend through and attach the layers.

15. The system of claim 7 further comprising a plurality of protective sheets that fully enclose the inspected structure, the protective sheets having an opening for an aperture of the infrared camera.

16. The system of claim 7, further comprising a grip configured to engage the protective sheet and the support at the same time, wherein the grip maintains the protective sheet in the orientation and the position.

* * * * *